United States Patent
Leijon et al.

(10) Patent No.: US 6,610,200 B1
(45) Date of Patent: Aug. 26, 2003

(54) SYSTEM AND ITS UNITS

(75) Inventors: Patrik Leijon, Uppsala (SE); Anders Tärnström, Uppsala (SE); Klaus Gebauer, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/830,843

(22) PCT Filed: Oct. 31, 1999

(86) PCT No.: PCT/SE99/01957

§ 371 (c)(1),
(2), (4) Date: Sep. 14, 2001

(87) PCT Pub. No.: WO00/25883

PCT Pub. Date: May 11, 2000

(30) Foreign Application Priority Data

Oct. 31, 1998 (SE) .............................................. 9803737
Nov. 8, 1998 (SE) .............................................. 9803813

(51) Int. Cl.[7] .............................................. B01D 15/08
(52) U.S. Cl. ..................... 210/198.2; 210/456; 210/656
(58) Field of Search ................. 210/635, 656, 210/198.2, 456, 289, 291

(56) References Cited

U.S. PATENT DOCUMENTS

| | | | | |
|---|---|---|---|---|
| 4,450,082 A | * | 5/1984 | Tanouchi ..................... | 210/656 |
| 4,871,463 A | | 10/1989 | Taylor et al. ................ | 210/161 |
| 4,976,865 A | | 12/1990 | Sanchez et al. ............. | 210/635 |

FOREIGN PATENT DOCUMENTS

| | | | | |
|---|---|---|---|---|
| DE | 278687 | * | 5/1990 | .............. 210/198.2 |
| DE | 19718652 A1 | | 4/1998 | .............. 210/198.2 |
| EP | 0 201 640 A1 | | 11/1986 | .............. 210/198.2 |
| JP | 63231262 | * | 9/1988 | .............. 210/198.2 |
| WO | WO 9520427 A1 | | 8/1995 | .............. 210/198.2 |
| WO | WO 9534359 A1 | | 12/1995 | .............. 210/198.2 |
| WO | WO 9833572 A1 | | 8/1998 | .............. 210/198.2 |

OTHER PUBLICATIONS

Translation of DD 278 687 PTO 03–2028 Mar. 2003 pp. 1–9.*

Translation of DE 19,718,652 PTO–03–2029 Mar. 2003 pp. 1–29.*

Translation of Japan Patent 63–231262 PTO 03–2030 Mar. 2003 pp. 1–19.*

* cited by examiner

*Primary Examiner*—Ernest G. Therkorn
(74) *Attorney, Agent, or Firm*—Royal N. Ronning, Jr.; Stephen G. Ryan

(57) ABSTRACT

This application discloses liquid chromatographic system including units selected from: a) a block (4) for distributing a liquid flow to a vessel (8), the characteristics being that there are through passing channels (7) comprising a narrow part (7a) and a widening part (7b), optionally with one check valve function per channel; b) a predistributor comprising a network of pipes starting at a pump (1), the characteristics being that the branches are narrowing down when going from the pump to the end pipes (3), and that each end pipes (3) have constriction means (19) providing for a significant pressure drop; c) a distributor with a distributor chamber (9) having an inlet pipe (11) equipped with sprinkler means (20); d) a tiltable chromatographic vessel (8) having a valve (15, 42) in its top and being possible to tilt 180° thereby facilitating emptying through the valve; the individual subunits and their use are also claimed.

12 Claims, 10 Drawing Sheets

Fig. 6a
Fig. 6b
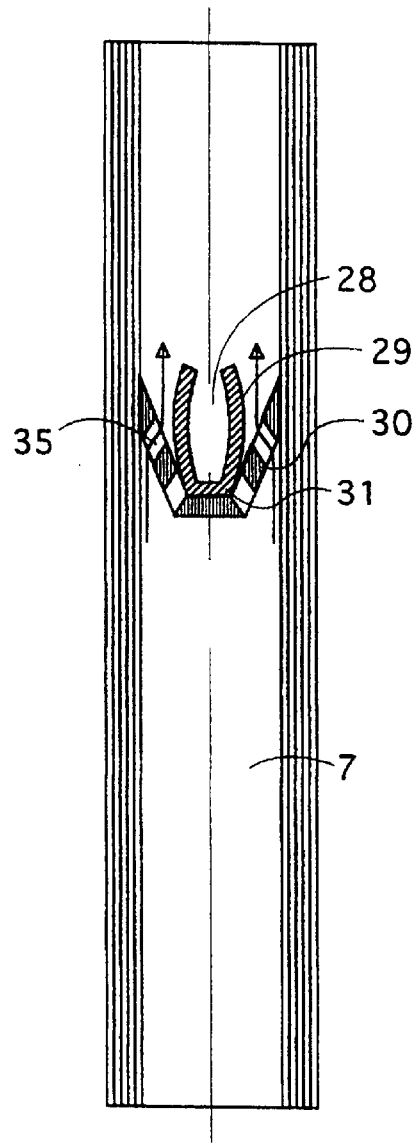
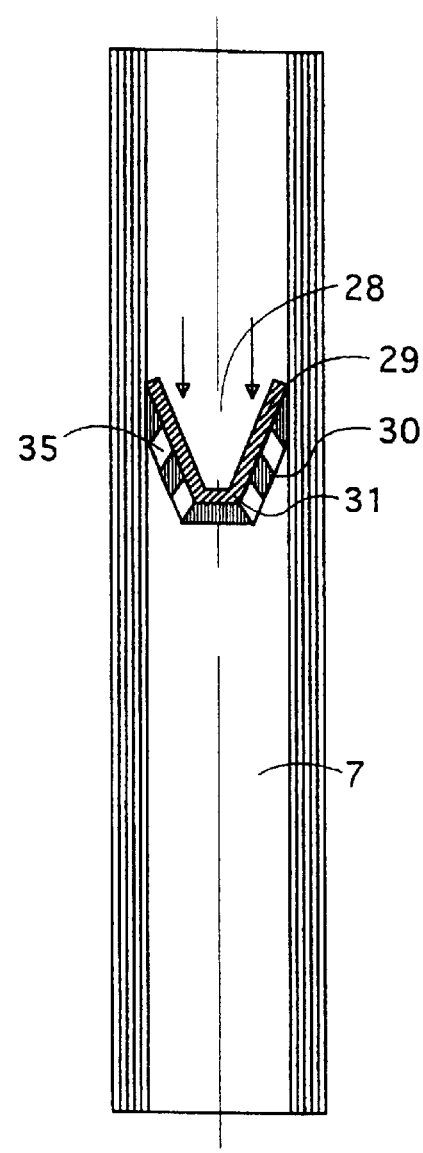

SYSTEM AND ITS UNITS

REFERENCE TO RELATED APPLICATION

This application is a 371 of PCT/SE99/01957 Oct. 31, 1999.

THE TECHNICAL FIELD

The present invention concerns a system for adsorption (capture) of a compound that is present in a liquid flow that pass through a fluidised bed. The invention also concerns various parts of this system, such the as a predistributor, a distributor, a vessel, a tilting device etc. The invention also concerns processes that are adapted to these parts.

By the term "capture" or "adsorption" is contemplated that the compound becomes bound to the particles of the fluidised bed by covalent bonds or affinity bonds, or by physically entrapment within the particles. The binding may be more or less reversible. Affinity bonds include binding caused by bioaffinity interaction, ionic interaction, hydrophobic interaction etc.

Binding as described above has previously been used for removal and/or purifying: a) the compound that becomes bound to the particles or b) a compound remaining in the liquid, or c) the liquid as such. In case of item a) the particles have been further processed in order to release and possibly further purify the bound compound. In case of items b) and c) the liquid has been further processed, for instance in order to recover or remove some other compound present therein.

Previous vessels for the above-mentioned processes have been in form of cylindrical columns equipped with meshes at the outlet end (collector end) and at the inlet end (distributor end).

The collector arrangement typically has contained a plate covered with a mesh on the side facing the vessel interior and a collector chamber with one or more outlet openings in the column end piece at the opposite side.

The distributor arrangement typically has contained a distribution chamber with one or more inlet tubes and a relatively thin perforated plate covered by a mesh resting on distance holders on the side facing the vessel interior. The major functions of the meshes have been to hinder fluidised particles from escaping the vessel and as a support for particles packed to a bed.

U.S. Pat. No. 4,450,082 describes a predistributor/distributor system for packed beds.

The meshes used at either end of the vessel have had pore sizes smaller than the particles used to form the bed (packed bed or fluidised bed).

Particles with densities greater than the liquid have been combined with upward flow and with the distributor placed at the lower and the collector at the upper end of the vessel. Particles with densities lower than the liquid have been combined with downward flow and with the distributor placed at the upper and the collector at the lower end of the vessel. After adsorption in a fluidised bed mode the particles have been allowed to sediment before release of the captured (adsorbed) compound (packed bed mode).

The term "release" includes desorption.

Capture of compounds in beds that are fluidised by an upward liquid flow is described in WO 9100799 (Upfront Chromatography), WO 9218237 (Amersham Phamacia Biotech AB), WO 9520427 (Amersham Pharmacia Biotech AB), WO 9717132 (Amersham Pharmacia Biotech AB), WO 9833572 (Amersham Pharmacia Biotech AB) and U.S. Pat. No. 4,976,865 (Sanchez et al, CNRS).

Drawbacks of Previous Techniques (Distributor Design)

In many applications a severe blockage has been experienced of the inlet and outlet meshes. The main reason has been clogging of feed material into the meshes, e.g. cells, cell debris, aggregates etc. This leads to an increased back pressure and maldistribution of the incoming fluid. The effect will be channeling in the bed disturbed plug flow and eventually the bed will collapse.

I similar effect is caused by air bubbles that are present in the feed stream.

Meshes have a mechanical instability. Even if installed as planar, they will tend to stretch and become wavy-like. Non-planar meshes tend to disrupt a plug flow profile created by a traditional distributor.

Distribution system in existing columns contains horizontal surfaces. It has been experienced that this type of surfaces often are difficult to clean from adhering material, for instance cell and cell debris in case the feed material contains fermentation broths and the like containing sticky components. Critical column parts are the horizontal surface of the bottom end piece and surface of the perforated plate (distribution plate) facing the bed where there are "dead zones", i.e. zones with no active flow of liquid and consequently no continuous rinsing.

Drawbacks Without Predistribution

When the area of the distributor is increased and/or the distributor area is divided into modules with separate distribution chambers, there is a risk for uneven distribution of flow across the area of the distributor. This problem becomes particular important in case plug flow is desired in fluidised beds.

Drawbacks of Prior Art Vessel Designs With Respect to Emptying

The traditional way of emptying vessels used in packed bed as well as in fluidised bed has been to empty either from the top or from the bottom while keeping the vessel in an upright position. Bottom emptying many times has been trough a valve in the side wall just above the bottom. Previous methods have been rather complicated, many times leaving bed residues in the vessels requiring extra cleaning.

Drawbacks of Previous Designs of Reactor Vessels (Fluidised Mode Versus Packed Bed Mode)

If the bed is eluted and/or washed in an expanded mode the volume of liquid needed will typically be at least twice the packed bed volume, i.e. much more than for the same procedure in packed bed mode. The reason is that the liquid in an expanded bed will be highly turbulent when a lighter buffer is trying to displace the denser sample. In respect of process economics, the consumption of washing buffer should be kept as low as possible.

The Objectives of the Inventive Aspects

To get a sanitary distributor design with a minimum of dead zones and horizontal surfaces.

To generate the essential plug flow profile without using a thin perforated plate and a mesh in which the pore size is less than the particle size.

To reduce the risk for blockage of the distributor system by increasing the smallest passage area considerably compared to columns in which meshes are included.

To facilitate plug flow characteristics in chromatographic beds.

To get a simple and mechanical robust construction which can stand an industrial environment.

To be scaleable (consistent performance) from small laboratory columns/vessels to industrial columns/vessels.

To have systems in which the need for large volumes for washing and for release is lowered by making it easier to change from packed to fluidised mode and the reverse.

To provide a system that facilitates emptying of vessels used for capturing compounds to particles in packed or fluidised bed mode.

By the term "essential plug flow" is contemplated a plate number $\geq 5$ for an expanded bed/fluidised bed. The method for measuring plate number is given in the experimental part.

BRIEF DESCRIPTION OF THE DRAWINGS

All figures are cross sectional views, either from one side, from above or from below. Parts in different figures having analogous functions have the same reference numerals.

FIG. 1a is a side view and FIG. 1b is a view from above at the indicated level.

FIG. 2a is a side view and FIG. 2b is a view from above at the indicated level.

FIG. 3a is a side view and FIGS. 3b is a view from above at the indicated level.

FIG. 5a is a side view of the vessel with no check valves shown, FIGS. 5b–f are blown up side views (b, c and f) or a view from above (d) and from below (e). FIG. 5b shows the top part of the vessel, FIG. 5c one alternative for a check valve, FIG. 5d a section of the distributor, FIG. 5e the branchings in a network of pipes in a predistributor and FIG. 5f a constricted part of the pipe net-work.

FIGS. 6a–b show the design of an alternative check valve in an open and a closed position, respectively.

The term "cross sectional area" means an area that is perpendicular to the flow direction, if not otherwise specified.

DESCRIPTION OF THE PREFERRED EMBODIMENTS

System aspects: One main aspect of the invention is a system suitable for the capture of a compound present in a liquid by particles of a fluidised bed. The characterizing feature is that the system comprises at least one unit of the inventive system described herein.

The distributor and the tilting device of the invention can be used with vertical flow that can be either upward or downward. The predistributor can be applied also to other flow directions.

The predistributor and distributor can also be used for beds in form of porous monolithic plugs. The predistributor will also function for packed beds.

Process aspects: These relate to processes for removal and/or purifying a compound from a liquid by allowing the liquid to flow through a vessel containing a fluidised bed of particles that are capable of capturing the compound. The characterizing feature is to use one or more units of the inventive system described herein.

Some of the process aspects will also be useful in packed beds and porous monolith beds in form of plugs. See below.

The liquids used may be aqueous, i.e. water or mixtures containing water and one or more water-miscible liquids. Also non-aqueous liquids may be used.

General Description of the Predistributor

Figure 3A:
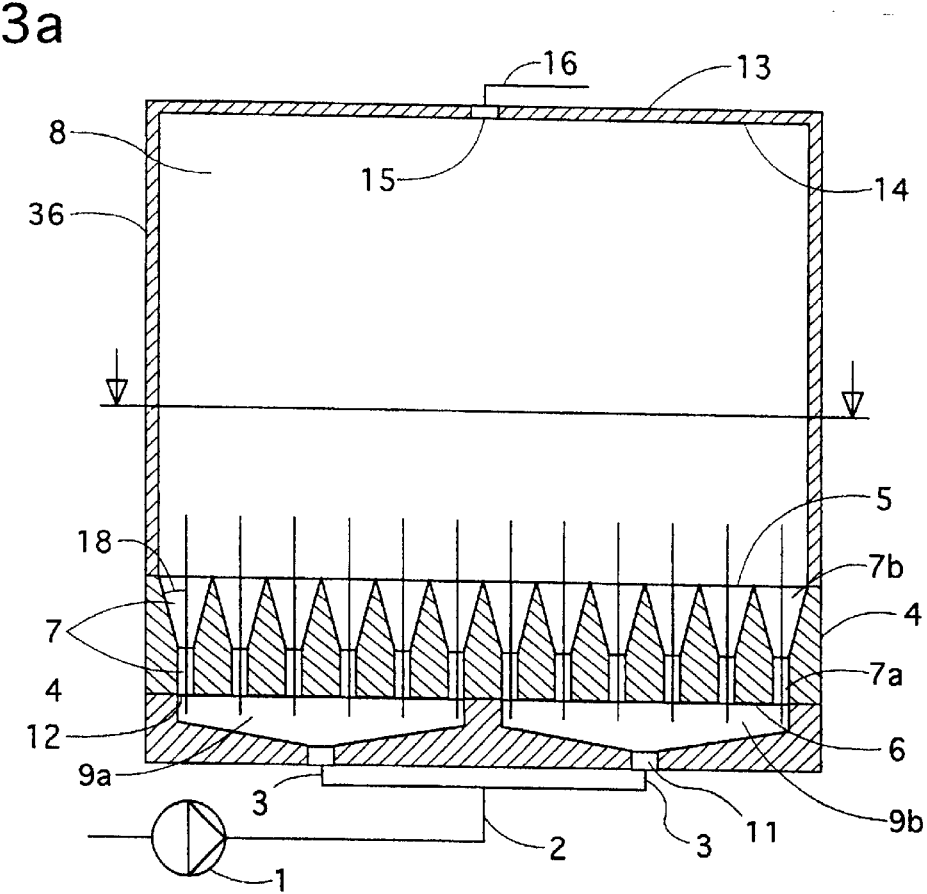
FIGS. 3a–b show a system containing a squaric vessel with a multi-channel four-module distributor variant and a predistribution system.
Figure 3B:
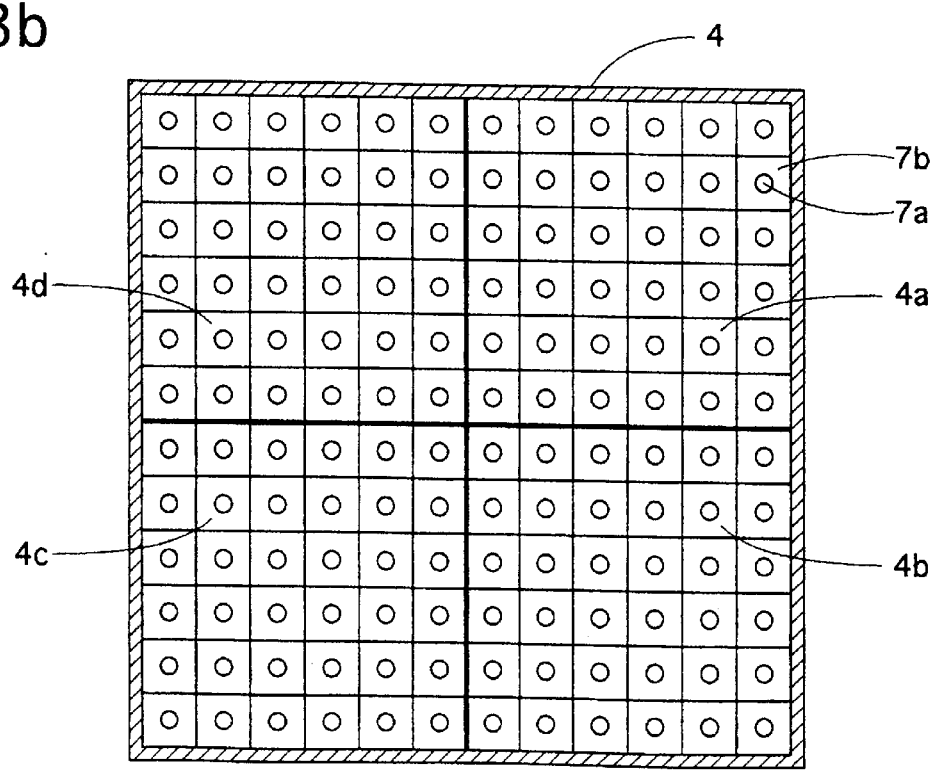
Figure 4:
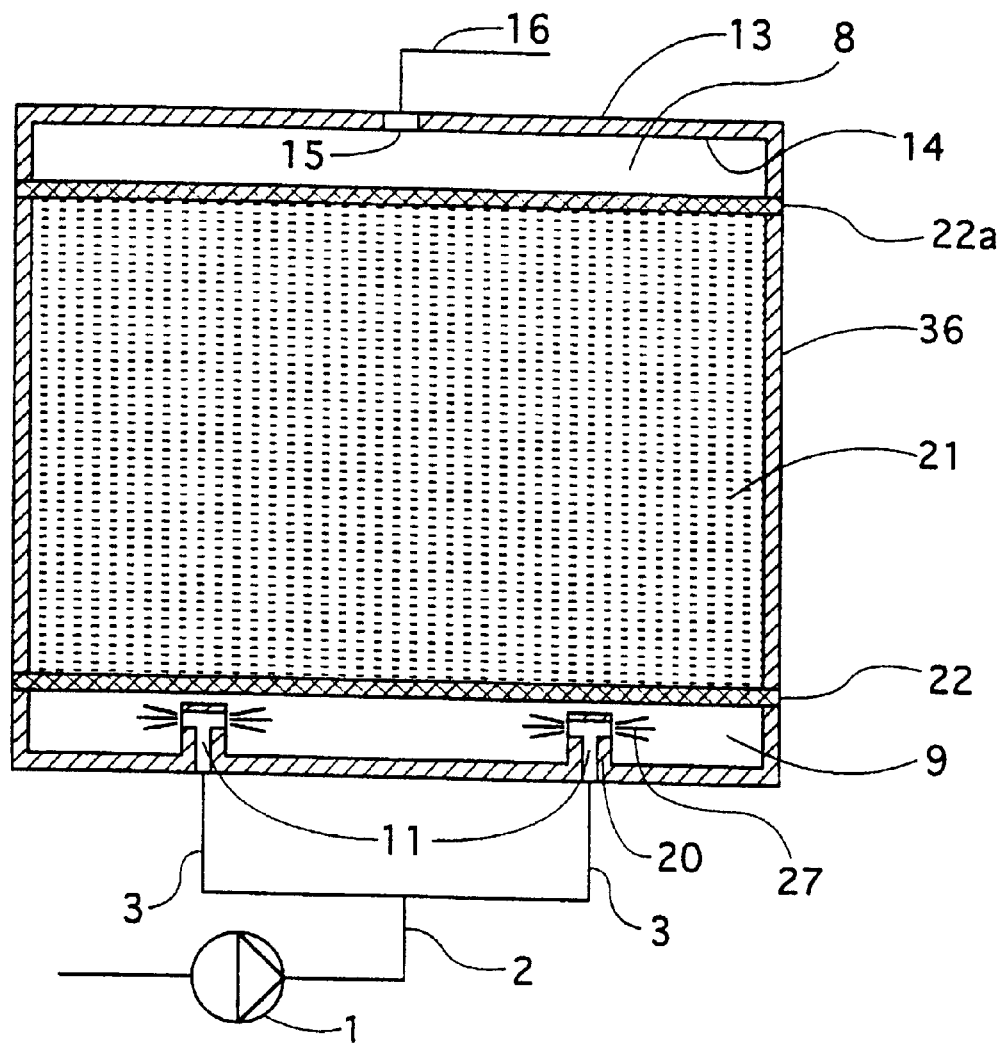
FIG. 4 shows a system containing a vessel with circular (column) or squaric cross sectional area having a traditional one-module distributor variant and a predistributor.

The predistribution system of the invention is illustrated in FIGS. 3–5. The system comprises a pump (1), a common inlet tube (2) branching into two or more open end pipes (3) directing flow to a respective subarea of a distributor. The characterizing feature is that there are means associated with each end pipe, which constrict the flow such that a significant pressure drop is created across the end pipes when the liquid is passing through.

In the context of the predistributor "pipes" or "pipe" designates flow passages in general. The terms include channel(s), tube(s), conduit(s) and other kinds of flow passages that have the analogous function.

General Description of the Distributor

The inventive distributor is illustrated in FIGS. 1–3 and 5. The distributor is built up of a block that may have a size from true plate dimensions up to true block dimensions. Open channels for liquid flow are passing through the plate. Thus the inventive part of the distributor is a distributor block (4) having one outlet side (5) and one inlet side (6) that are essentially parallel to each other. Between the two sides there are one or more evenly spread out essentially parallel identical open channels (7) that are perpendicular to the two sides (5,6) and stretching from one side to the other. The characterizing feature is that each channel (7) comprises a narrow inlet section (7a) next to the inlet side (6) of the distributor block (4) and an outlet section (7b) which is widening towards the outlet side (5) of the distributor block (4).

The Distribution System

The distribution system comprises the inventive distributor and optionally a predistributor that may be our novel predistributor.

Figure 1A:
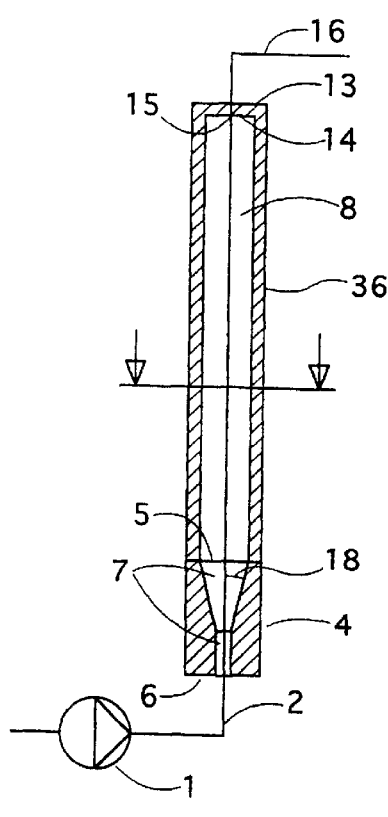
FIGS. 1a–b show a system containing a cylindrical vessel with a one-channel one-module distributor variant.
Figure 2A:
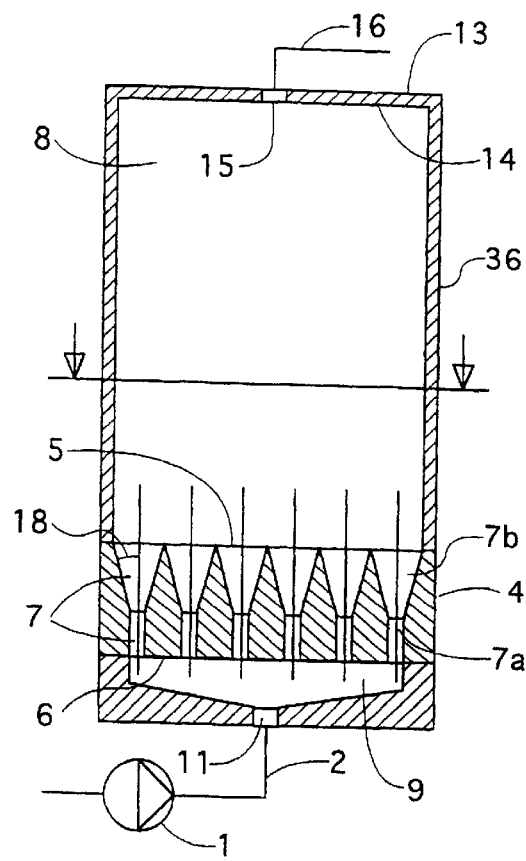
FIGS. 2a–b show a system containing a squaric vessel with a multi-channel one-module distributor variant.
Figure 1B:
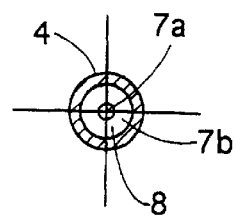

Three versions of our distribution system are shown in FIGS. 1–3.

FIG. 1 shows a one-module distributor variant applied to a small cylindrical vessel (8). In principle no predistribution is required. This variant is primarily intended for thinner vessels/columns, for instance with cross sectional areas corresponding to squares with sides $\leq 20$ cm. FIG. 2 shows a one-module distributor variant intended for larger vessels (8), for instance with cross sectional areas corresponding to squares with sides $\geq 10$ cm. A predistributor is normally not required. FIG. 3 shows a variant in which the distributor is modular, i.e. contains two or more equal parts (modules) each of which having its own distribution chamber (9a–d, only 9a–b shown) and distributor block (4a–d). To this variant of the distributor there should be connected a predistribution system which divides and distributes an incoming liquid flow to different modules/subareas of the distributor. Modular distributors are intended for larger vessels, for instance with cross sectional areas corresponding to squares with sides $\geq 40$ cm. The number of modules in one distributor depends primarily of the size of the vessel, and may for instance be 4, 16, 64 etc. in case the column is squaric.

FIGS. 1–3 further show a common inlet conduit (2) with a pump (1), a predistributor (in FIG. 3 only represented by a branching of the inlet conduit into the end pipes (3)), one or more distribution chambers (9 and 9a–d, only in FIGS. 2 and 3, respectively) with an inlet opening (11, FIGS. 2 and 3) and one or more outlet openings (12), a distributor block (4) with one or more channels (7), and the vessel (8) to which the liquid is to be distributed. Across the vessel from the distributor end there is the collector arrangement. In FIGS. 1–3 the collector arrangement is illustrated with a relatively simple construction consisting of the inner side (14) of the end piece (13) and a central outlet opening (15) connected to an outlet tube (16). The opening (15) may be equipped with a valve function. The incoming liquid will pass the parts of the vessel in the same order as they are written above.

The channel/channels (7) in the distributor block (4) enables/enable liquid flow to enter the vessel (8) from the incoming conduit without any distribution chamber (FIG. 1) or via a distribution chamber (9 and 9a–d, FIGS. 2 and 3, respectively). Each channel (7) has a narrow inlet section (7a) starting from the inlet side (6) of the distributor block (4) and an outlet section (7b) widening towards the outlet side (5) of the distributor block (4).

The cross sectional area of the narrow inlet section (7a) is typically circular although also other geometrical forms may be used.

The length of the widening (7b) should be such that the outlet of the channels (7) covers as much as possible of the outlet end area (5) of the distributor block (4).

The widening outlet section (7b) may be conical, pyramidal etc and forms therebetween. The widening may start as a cone with a circular cross sectional area closest at the narrow inlet section (7a), then continuously change to a rectangular area, such as a squaric area (17, 7b in FIGS. 2b and 3b). The widening angle (18), i.e. the angle between the wall of the widening outlet section (7b) and the intended flow direction, may be from just above zero, e.g. >0.5°, such as >2–30, to <75°, such as $\leq 50°$ or even $\leq 20°$. In order to optimize for plug flow in the channel outlet areas the angle should be rather smooth with an angle $\leq 20°$, such as $\leq 10°$, with preferred values typically being around 5–8°. The widening may be symmetrical or unsymmetrical around the central axis of the channel.

The ranges for the angels given above primarily refer to the angel at the borderline between the narrow inlet section (7a) and the widening outlet section (7b). At the opening rim in outlet side (5) the angels can be considerably higher. Preferably the angel should be continuously increasing when going upwards toward the outlet surface (5) (convex surface). In this variant the starting angel at the interior of the widening section (7b) may be as low as zero and then increase in the lower part of the widening section (7b) in order to facilitate the formation of early plug flow. The shape of outlet section (7b) may be bell-like (continuous line) or preferably trumpet-like (broken line). See FIGS. 11a and b. The widening section (7b) may change form (both along the Y-axis and in the x-y-plane) at the outlet side (5) in order to accomplish an optimal dense packing of the opening areas (17) in the outlet side (5).

Channel outlet areas (17 FIGS. 2b and 3b) that are squaric or hexagonal or of any other form permitting edge-by-edge packing are preferred. The reason is that the openings then will be able to occupy essentially 100% of the area of the outlet side of the distributor block facing the interior of the vessel. This geometrical arrangement will also assist in optimizing for plug flow across the cross sectional area at the outlet side (5) of the distributor. A squaric, hexagonal etc form of the full outlet side (5) of distributor block or modules thereof is therefore preferred.

Larger widening angels, for instance >10° such as >15°, will often require a higher density of channels and channels with thinner narrow sections (7a) in order to create a pressure drop over the block/plate (4) for sufficient plug flow characteristics in the expanded bed.

The low widening angle (18) and the pressure drop requirements for optimizing to plug flow close to the outlet side (5) of the distributor (4) imply that the distributor block typically will have true block dimensions. This is contrary to the prior art methods for flow optimisation, which has resulted in a thin plate character of the corresponding part of the distributor.

In case the narrow inlet sections (7a) are short compared o the widening outlet section (7b), an insignificant or obsolete pressure drop across the distributor block may be compensated by attaching pressure drop means (68a, 68a, 68b, 68b), FIG. 11) to each inlet opening (12). See further FIG. 11. This extra pressure drop means may be inserted as soon as the pressure drop across the distributor block (4) is not sufficient.

FIG. 3 shows a distributor built up of four modules (chambers 9a–d plus distributor blocks 4a–d). Each modules may be connected to one end pipe (3) of the predistribution system. In less preferred variants there may be two or more end pipes connected to each module. There may be a sprinkler arrangement in the inlet opening(s) of a distribution chamber (for instance as described (20) for the system in FIG. 4).

Figure 2B:
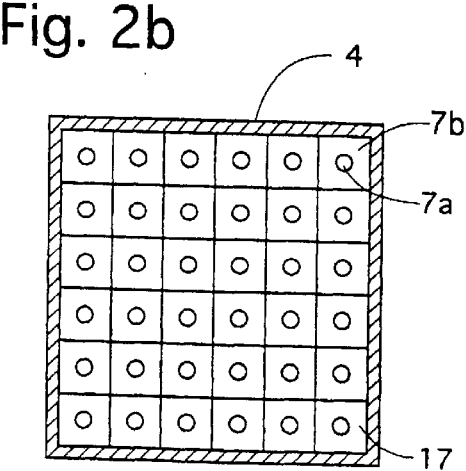

FIGS. 1b–3b illustrate that the cross sectional area of the vessel and the distributor may be circular (FIG. 1b) or squaric (FIGS. 2b and 3b).

FIG. 4 shows our novel predistribution system (10) applied to a larger vessel (8) that may be cylindrical (column) or have a rectangular, such as squaric cross sectional area. The vessel contains a matrix (21) that may be a packed bed or a porous monolithic plug. By the term "larger column" is contemplated that the cross-sectional area should be greater than for a column with a radie $\geq 20$ cm. The fluid communication between the distribution chamber (9) and the bed (21) is via a mesh (22), possibly combined with a thin perforated plate (not shown) with holes passing through the plate and placed between the mesh (22) and the distributor chamber (9). On top of the bed (21) there is placed a second mesh (22a). For this type of vessels one can envisage distributors consisting of modules each of which having their own distributor chamber and mesh, possibly combined with a distributor plate. The predistribution system is of the same type as shown in FIG. 3. For beds in form of porous monolithic plugs either or both of the meshes (22 and 22a) may be replaced with a perforated plate, for instance with a slot between the mesh and the inlet side of the bed. There are sprinkler means (20) in the distribution chamber (9).

Figure 11A:
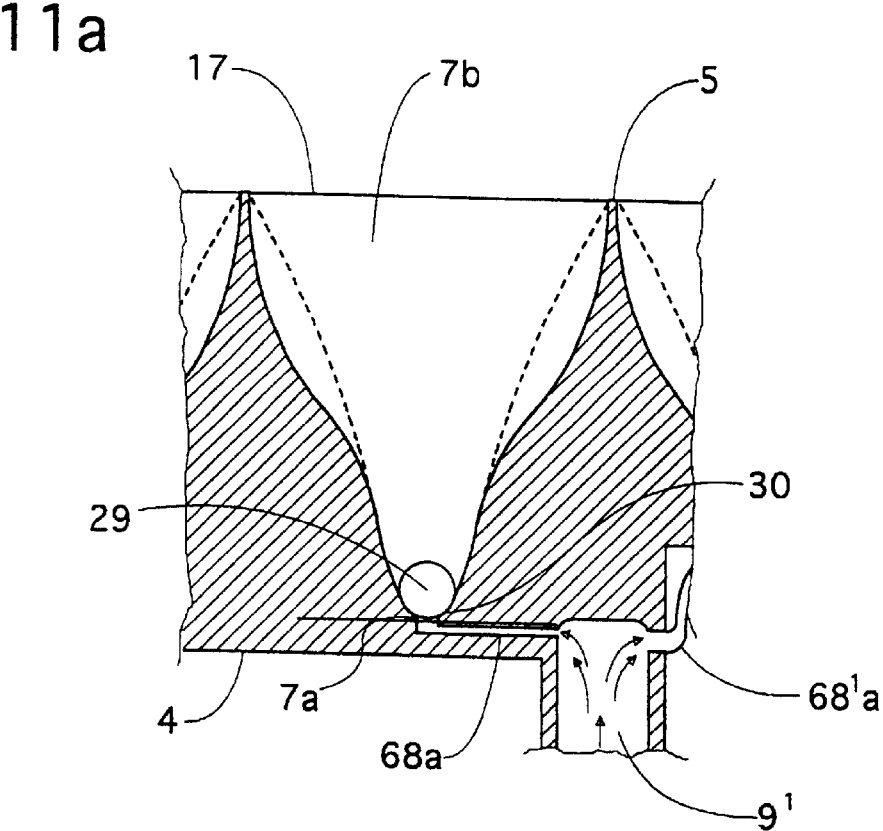
FIGS. 11a and 11b show alternative designs of the distributor block with a distributor chamber and liquid connections from the chamber to the block.
Figure 11B:
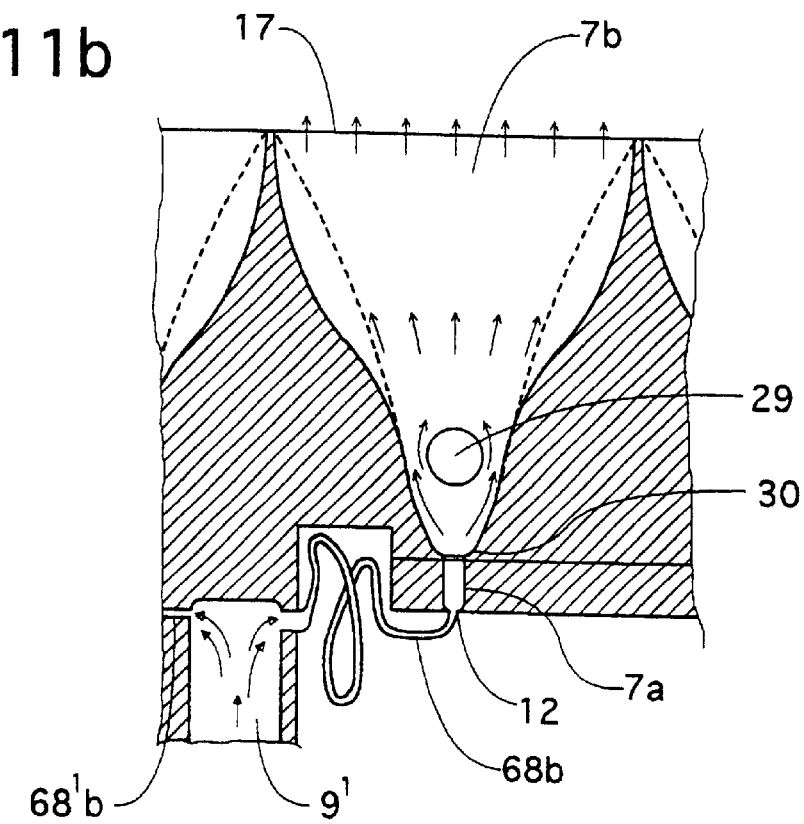

FIGS. 11 show an enlarged section of two alternatives of the distributor block (4). The alternatives have a widening outlet section (7b) that is convex in its lower part. A trumpet-like (broken line) and a bell-like (continuous line) shape are indicated. The narrow inlet section (7a) is relatively short and have a relatively large cross sectional area, which means that the pressure drop over the narrow inlet section (7a) in practice will be obsolete (null) or insignificant. This may be compensated by extra pressure drop means that in FIG. 11 is illustrated as a channel (68a), FIG. 11a) or as a tube (68b, FIG. 11b) that may be flexible. Also other alternatives for flow passage are possible. The flow passage (68a, 68b) connects the distribution chamber (9') to the inlet opening (12) of the narrow inlet section (7a). The distribution chamber (9') in turn may be connected to a pump and a liquid reservoir, possibly via a predistribution system (not shown) in analogy with the design given in FIGS. 2–3 and 5. The reference numerals 68'a and 68'b indicate additional flow passages between one and the same chamber (9') and other openings (12) in the block (4). Also this is in analogy with the connections between the distribution chamber (9, 9a, 9b . . . ) and the vessel interior (8) in FIGS. 2–3 and 5. The geometrical design of the openings (17) should permit dense packing in the outlet side (5) as discussed above for FIGS. 2–3 and 5. FIGS. 11a–b also illustrate that there may be a check valve in which the valve function may be based on a movable body (29). The check valve may also have valve closing means (30) and retaining means (not shown). For various designs of check valves see FIGS. 5c–d and FIGS. 6a–b.

Function of the Distribution System

The actual distribution of the liquid takes place in the distribution chamber (9). The liquid flow that enters the chamber from the predistribution system (10) will distribute evenly throughout the chamber due to the flow resistance in the narrow inlet section (7a) of the channels. This channel part is sized to provide a sufficient pressure drop in order to resist possible pressure fluctuations within the vessel (8). The widening angel (18) of the outlet sections (7b) of the channels is very smooth in the preferred variants in order to prevent energy losses due to creation of extra turbulence in the outlet of the channels, The end pipes (3) of the predistributor system (10) assist in distributing the liquid evenly to the subareas/chambers (9a–d) of the distributor and to the narrow inlet sections (7a). The final distribution into the vessel (8) is through the widening outlet sections (7b) of the channels.

Detailed Description of the Predistribution System

Figure 5A:
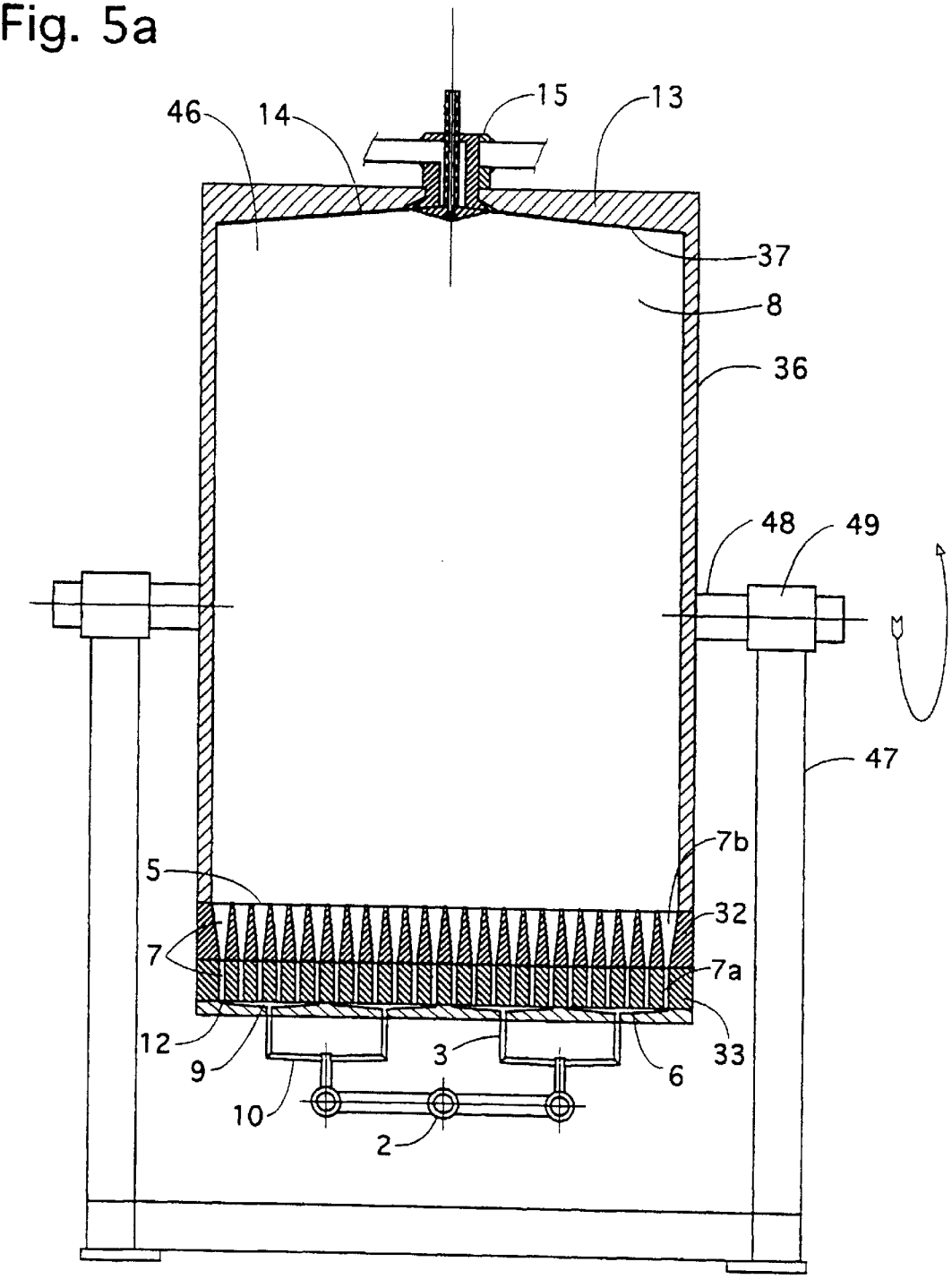
FIGS. 5a–f show a system containing preferred variants of the vessel, the distributor with check valves, the collector, the predistributor and the tilting device.
Figure 5B:
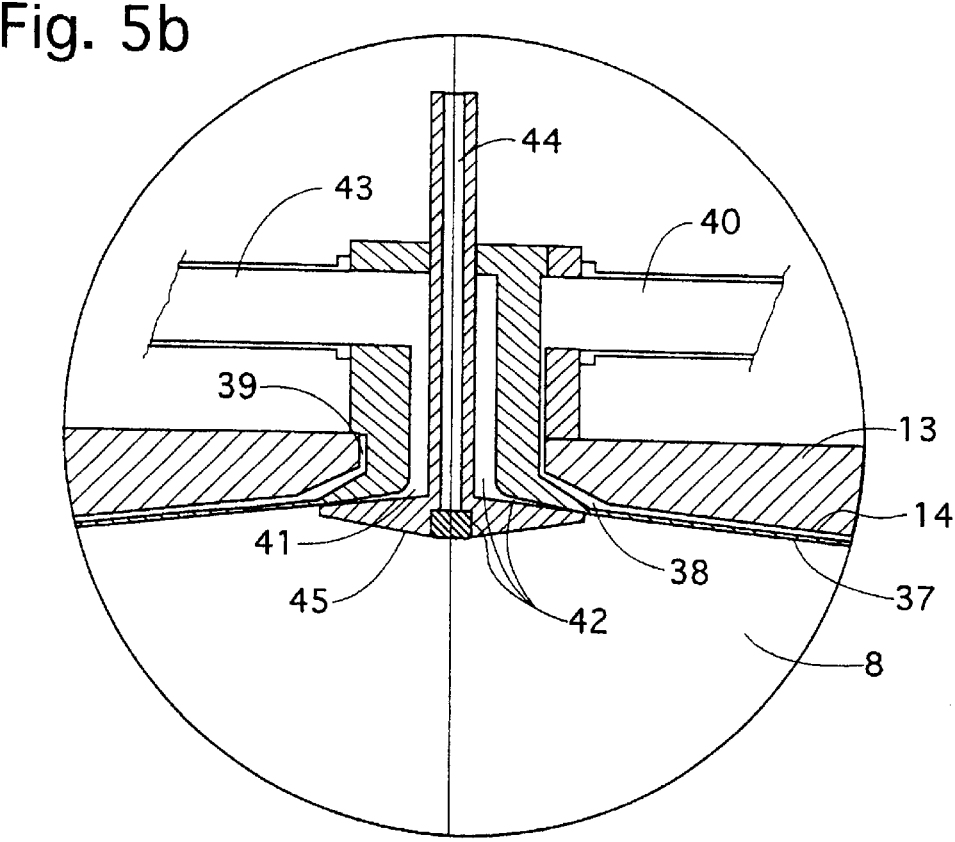
Figure 5C:
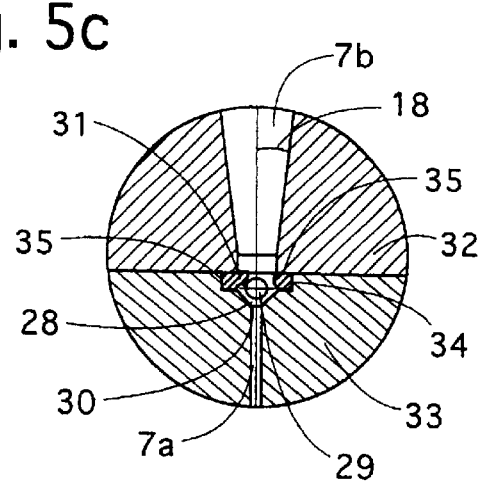
Figure 5D:
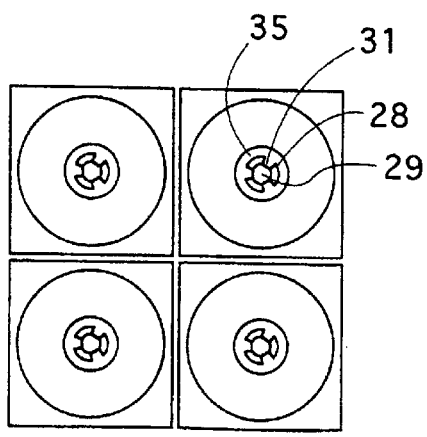
Figure 5E:
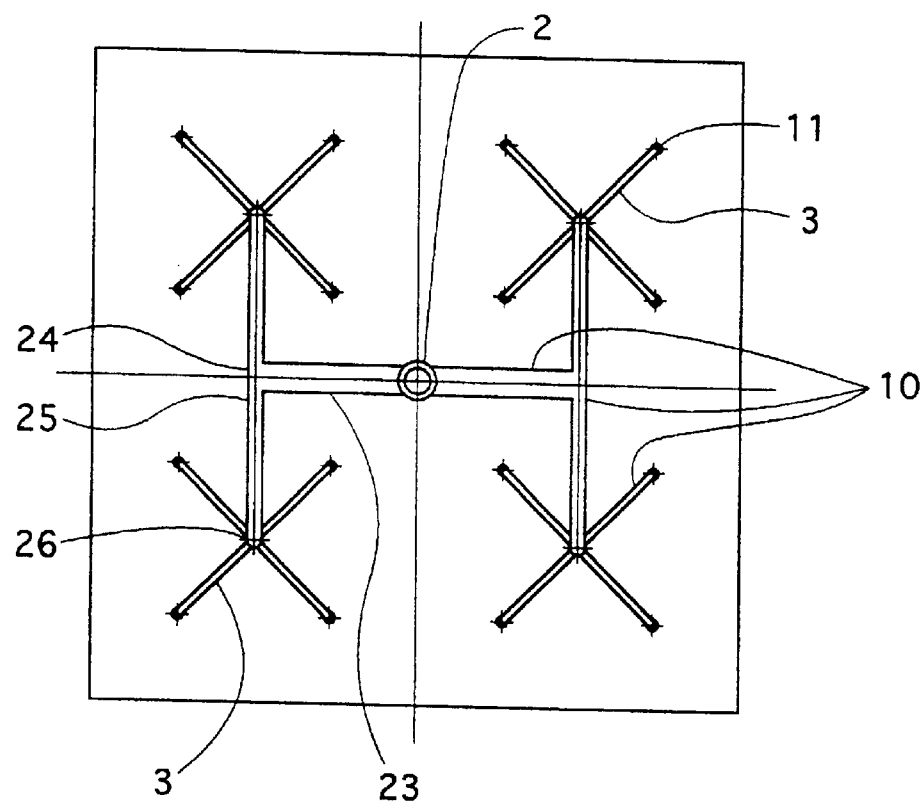
Figure 5F:
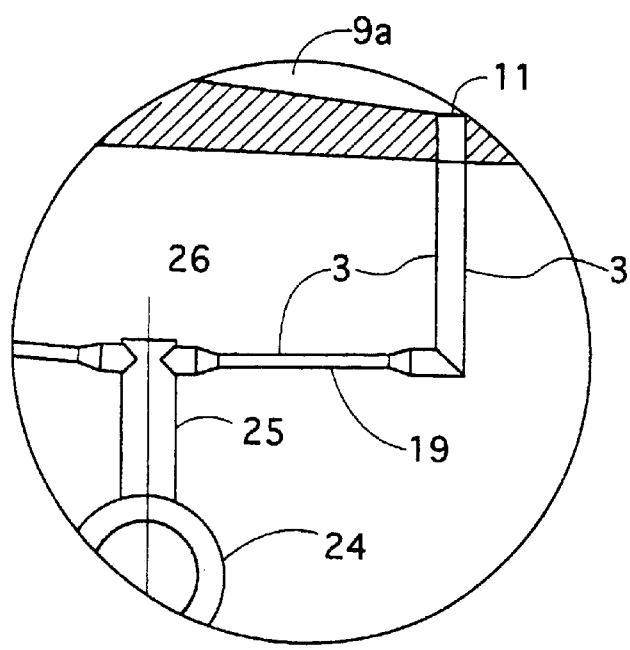

The details of the predistributor system are illustrated in FIGS. 5e–f. The predistributor is built up of a pipe network that comprises a pump (1, only shown in FIGS. 3 and 4), a branched network of pipes (10) ending in at least one pipe (3) per subarea of the distributor. Two types of "subareas" are illustrated in FIGS. 3 and 4:

a) the distribution chamber of a distributor module and b) the part area of the inlet end of a common distributor block, plate or mesh to which an end pipe (3) direct flow.

The various pipe branches are narrowed down when going from the pump (1) to the end pipe (3). See FIG. 5f where the inlet conduit (2) is thicker than the first pipe parts (23) that are thicker than the second pipe part (25) that are thicker than the end pipes (3). Numerals (24) and (26) represent branchings. The last piece of pipe (3) comprises, between its outlet (11) into the chamber (9) of a module and the last branching (26), a part (19) that has an inner diameter that is less than the rest of the pipes in the network. This constricted part (19) of each end pipe will create a significant pressure drop compared to all other pipe parts. The pressure drop will stabilise the distribution of liquid to the chambers (9a,b,c . . . ). Small pressure fluctuations within the distribution chamber(s) (9a,b,c . . . ) and the vessel (8) will not affect the distribution if the pressure drop is selected high enough.

The pressure drop over each end pipe should be essentially equal. This may be achieved by letting the end pipes have essentially the same length and inner diameter. Theoretically this may also be achieved for end pipes of different lengths in case the inner diameter is varied appropriately.

The pipe network may have branchings on several "levels", meaning that branches of the incoming conduit (2) in turn may branch one or more times before ending in an end pipe (3). See FIG. 3f.

Each narrow end pipe (3) may be equipped with sprinkler means (not shown) as described above in FIG. 4 (numeral 20).

Measures of Important Features

The pressure drops caused by the end pipes (3) and by the narrow inlet sections (7a) of the channels depend on i.a. flow rates. Typical flow velocities for fluidised beds are >25 cm/h. For higher productivities the goal is to go over at least 70 cm/h with the understanding that the higher velocities will require denser particles. At the present time a preferred range of 70–3000 cm/h can be envisaged. The pressure drop will increase with decreasing cross sectional area and increasing length of both the narrow inlet sections (7a) of the channels and the constricted parts (19) of the end pipes. Increasing number of channels (7) will decrease the pressure drop.

Typically the cross-sectional area of the narrow inlet sections (7a) will correspond to a circle having a diameter selected in the interval 0.1–20 mm. The preference is for 0.4–10 mm. The cross-sectional area is preferably in form of a circle. The length will typically be in the interval 1–500 mm, with preference for 1–200 mm. The number of channels per distributor module are preferably such the their outlet areas (17) are as dense packed as possible. Typical desired pressure drop values for the narrow inlet sections (7a) are often selected in the interval 10–10000 pascal. An insufficient pressure drop may be at hand in case the narrow inlet sections (7a) have a length and a cross-sectional area that correspond to the lower respective upper part of these ranges. In these cases an insufficient pressure drop may be compensated by connecting separate pressure drop means to each of the openings (12).

The cross-sectional area of the constricted part (19) of end pipes (3) should correspond to a circle having a radie in the interval 1–50 mm, with preference for 3–30 mm. The length of the same parts is in the interval 1 cm–1 m, such as 5 cm–30 cm. The cross-sectional area is preferably in form of a circle. Typical pressure drop values are in the interval of 100 pascal–2 bar.

These values and features also apply, where appropriate, to predistributors and distributors to be used for packed beds and porous monolithic plugs.

The above-mentioned features are interrelated in a complex way and are also dependent on the size of the vessel, the type of bed, distributor area, distributor chamber design etc which means that they need to be decided on a per case basis. As a general rule of thumb the pressure drop over the end pipes (3) should be much higher than the pressure drop over the narrow outlet sections (7a), for instance more than 5 times, often more than 10 times.

Distribution Chamber With Sprinkler Means

This variant is illustrated in FIG. 4. It is a distribution chamber (9) having one (2, FIG. 2) or more (3, FIG. 4) inlet conduits. The chamber (9) is in liquid communication with a vessel (8) intended for carrying a chromatographic medium (21) in form of particles as defined above or in form of a monolithic plug having flow through pores. The means for liquid communication between the interior of the vessel and the distribution chamber may be via a net/mesh (22) possibly combined with a perforated plate or block having open through passing channels. The net/mesh is in the latter case positioned between the interior of the vessel and the perforated plate or the block. Liquid communication may also be via our inventive distributor block without any net or mesh. The characteristic feature is that each inlet conduit (11) is equipped with sprinkler means (20). Typically the end of each inlet conduit (11) has a cap and holes (27) placed circularly in the wall of the end of the conduit just before the cap. The holes should permit even radial distribution of incoming liquid. The distribution should be perpendicular to the flow direction in the conduit concerned. The size, amount and total area of the holes are selected such that there will be an increase in flow velocity when the liquid is passing through the holes.

The inlet conduit (11) may be one of the end pipes (3) in the inventive predistribution system described herein (see FIG. 3) but equipped with sprinkler means (20). The inlet conduit may also be the common inlet (2) to the distribution chamber of a one-module distributor of the inventive type (FIG. 2) or of the corresponding conventional type for fluidised beds.

The primary advantage of this construction is that it will facilitate even distribution of liquid to channels (7) and possibly assist in keeping the chamber clean from sticky components that may be present in the feed material.

Distributors With Check Valve

The distributor in this aspect comprises a block/plate which has two essentially parallel planar sides (5 and 6, respectively) and one or more, preferably two or more, parallel open channels (7) that are perpendicular against the sides (5,6). When in use the block/plate is placed in the inlet side of a chromatographic vessel as described above. The inventive distributor/block in this aspect of the inventive system is characterized in that each channel is equipped with a check valve, for instance as described below.

The number of channels and their, size, length and form should be selected to enable plug flow as described above. In case the channels contain no widening, the length and width of the channels can be selected as outlined above for the narrow inlet sections (7a). Appropriate pressure drops are in the interval 10–10000 pascal. If needed the channels may be combined with extra pressure drop means as discussed above. See for instance FIG. 11.

Preferred Distributor Blocks

In a preferred distributor variant (illustrated in FIGS. 5a,c,d) each channel comprises a check valve function, preferably located between the narrow inlet section (7a) and the widening outlet section (7b) or in the lowest part of widening outlet section. This function comprises a part of the channel (check valve space) (28). The check valve space (28) is equipped with valve means that keeps the channel open when forward flow is applied and closed when no flow or back flow is at hand. The check valve space may be a recess (28) coaxial with and located at the exit of the narrow inlet section (7a) next to the start of the widening outlet section (7b). The valve means may comprise a body (29) that has such a size and form that it is movable within the check valve space (29) and permits liquid to pass between the body and the walls of the check valve space (part of the channel walls). The body is movable within the check valve space between a) a first position which contains valve closing means (30) that, when the body is engaging this means, the channel will be closed, and b) a second position at which the movement of the body is stopped by so called retaining means (31) thereby preventing the body from escaping the space and enter the vessel while permitting flow to pass through.

The valve means in a preferred variant thus comprises the movable body, the closing means and the retaining means.

The means in the first position may be a smoothly constricted part of the check valve space, for instance its bare inlet opening (30). The retaining means may be protrudes (31) attached to the outlet opening of the check valve. Exemplary protrudes are pegs, indentations, a net or the like which will catch or prevent passage of the body. An alternative for protrudes are means that anchor the body (29) to the check valve space (28). In this case the retaining means may be elastic or resilient anchors, for instance string-like. For still another alternative see FIGS. 6a–b. The liquid that is to pass through the check valve often contains sticky particulate materials. This means that the retaining means and closing means shall occupy as little as possible of the cross sectional area of the check valve space.

The movable body is selected to have a size and form such that it a) together with the closing means (30) in the first position is able close the channel (7), and b) when moved to the second position, can not pass through but still permit liquid to pass through.

The size and form of the body, the closing means and the retaining means should be selected such that the body is able to move from one position to the other by changing from forward flow to no flow or to back flow or the reverse. Opening and closing may also be controlled by external means.

The movable body (29) may have various physical shapes, such as pyramidal, spherical, conical, sheet-like etc. The proviso is that the selected form should be able (a) to match tightly to the the closing means and (b) to be retained by the retaining means without preventing flow to pass by.

In case the flow is upward, it is preferred to select a body (29) having a density greater than the density of the liquid used. The flow pressure will lift the movable body (29) and free it from the closing means (30) of the check valve space (28). When flow is stopped or back flow is at hand the gravitational force and/or back flow will press the body (29) to the closing means (30) thereby closing the valve. In case the flow is downward it is preferred to select a movable body (29) that has a lower density than the liquid. The same principles apply in this variant as in the case with upward flow. Downward flow will open the valve. When downward flow is stopped the buoyancy force of the liquid will close the valve. One can also select to drive and/or support the closing and opening functions by external means, such as magnetic and mechanical means.

In a preferred variant (also shown in FIGS. 5a–c), the distributor block may comprise two block parts: the inlet block part (33) comprising the narrow inlet sections (7a) and the outlet block part (32) comprising the widening outlet sections (7b) of the channels (7). The different channel sections are equally spaced in their respective block part so that, when the outlet block part (32) is placed on the inlet block part (33), channels (7) can be formed. In case check valve spaces (29) are to be included they may be formed as a respective recess coaxial with a channel opening in one of block parts (32,33) or formed from a recess in each of the block parts (32,33). Valve means, such as a movable body, retaining means and closing means may then be located to the recesses as found appropriate.

In one check valve variant the retaining means is a tightening sheet material placed between the block parts (32 and 33). This sheet material may have holes matching the channel part openings in respective block part. The peripheries of the holes are then equipped with retaining means in form of protrudes, pegs, indentations and the like as described above. A similar effect may be achieved as illustrated in FIGS. 5c–d by having the rim of the recess equipped with a minor recess (34) in which an o-ring (35) is placed. The o-ring may be equipped with inwardly directed retaining means (31).

Another alternative construction of the distributor block is to manufacture it from three block parts: one inlet part comprising the narrow inlet sections, one middle part comprising the check valve spaces and one outlet part comprising the widening outlet sections.

Manufacturing of the distributor block from block parts is also applicable to distributors without check valve function.

Tightening between the different block parts may be achieved in a manner known per se, for instance by placing the tightening resilient sheet material or o-rings between the various block parts as described above.

An alternative check valve with a movable body is shown in FIGS. 6a–b. FIG. 6a shows the valve in an open position and FIG. 6b in a closed position. This check valve comprises a check valve space (28) that is part of a channel (7). The closing means is a more or less cup-like structure (30) firmly placed in the check valve space with its open end turned downstream in the direction of the vessel (8). The structure (30) has flow through holes (35) and/or provides a space between its periphery and the channel wall. On the downstream side (concave side) of the structure (30) is placed a movable body (29) in form of a resilient sheet that is able to tighteningly cover this side of the structure and possibly extending a bit up on the channel wall. At forward flow (FIG. 6a) the sheet is bent forward opening the flow through passages (35). At zero or back flow (FIG. 6b) the resilient sheet returns thereby tightening the flow through passages (35). In this variant the cup-like structure (30) functions as closing means and the part of the body attaching the body to the structure as retaining means (31). The inlet and outlet of the check valve space becomes redundant in the simplest variant. This type of check valve is particularly adapted to be placed in the narrow inlet section (7a) of the channels.

The check valve space (29) may be located (a) between the narrow inlet section (7a) and the widening outlet section (7b), (b) in the narrow inlet section (7a) or in close proximity thereto in the distribution chamber, and (c) in the widening sections (7b).

Alternative c) means that the check valve space (29) may be located close to or in the vessel (8). However, the closer to the vessel (8), the retaining means is located the higher the risk for disturbances in plug flow. In case the retaining means is located in the vessel and the body is non-anchored, the spaces between the retaining means and the rims of the openings of the widening section have to be less than the size of the body. For retaining means in form of nets, the meshes shall be smaller than the body.

The various block parts used in the distributor block of the invention may be manufactured from plastics, such as polypropylene, or metal material, such as stainless steel. The various channel parts may be formed by the use of, for instance, a laser, water drilling, or mechanical drilling or combinations thereof. Water drilling in combination with mechanical drilling is experienced to be a particularly good variant for plastics. The sheet material placed between block parts of the distributor may be manufactured from elastic and/or resilient materials, such as rubber.

The movable body may be manufactured from steel or glass or plastics, while remembering selecting material so that the body can move correctly when flow is applied or disrupted.

The Vessel Used for Capture

The adsorption vessel is defined by a distributor block (4 in FIGS. 1–5) at the inlet, a collector arrangement at the outlet and walls (36) between the collector arrangement and the distributor block. The walls are perpendicular at least in relation to the distributor block. The distributor may be of the same type as described above for our inventive distributor. See FIGS. 1–3 and FIG. 5a. In some variants the distributor may be a mesh. See FIG. 4. The size and form of the cross sectional area of the vessel should be the same as for the distributor block i.e. circular, rectangular (such as squaric), hexagonal etc. See above.

The collector arrangement may be of the conventional type. It may also be as suggested in FIGS. 1–3.

FIGS. 5a–b illustrate that the collector arrangement may comprise an end piece (13) and a mesh (37) on the side (14) facing the vessel interior. A perforated plate may be placed therebetween (not shown). Between the end piece and the mesh there is a slot (38). The side of the end piece (14) facing the mesh (37), the mesh (37) and, if present, the perforated plate may have a slightly conical form turning outward from the vessel interior and fitting physically into each other as shown in FIGS. 5a–b. In order to maintain the slot (38) well-defined, the end piece surface (14) towards the vessel interior may have ridges or other protrudes. (not shown) on which the mesh is resting. Both the mesh (37) and, if present, the perforated plate is covering essentially the complete area of the outlet end of the vessel. The slot (38) may have an opening (39) in the end piece (13), which in turn is connected to an external tubing (40) for guiding liquid away from the vessel when the vessel is run, for instance with particles in fluidised mode. The mesh (37) and, if present, also the perforated plate may have an opening (41) that are connected to an opening in the end piece. This opening in the end piece may be the same as opening (39). The opening (41) may carry a valve (42) and a thereto separately linked external tubing (43) for unloading and loading the vessel, for cleaning purposes, and/or for letting the liquid flow out during fluidised bed operations (for instance capture, washing, releasing, equilibration and cleaning). The valve may be a nozzle, for instance constructed as described in U.S. Pat. No. 5,213,683 (Chromaflow) and U.S. Pat. No. 5,282,973 (Chromaflow) and WO 9810451 (Euroflow) which are hereby incorporated by reference. The external tubings (40 and 43) may contain one or more two-way and/or three-way valves.

The valve (42,15) shown in FIGS. 5a–b can be envisaged particularly useful in the context of present inventive distributor design. It has two positions (open and closed) and may contain a movable piston like device (44) equipped with a disc (45) and placed in opening (41). The disc has such a form and size that it will tighten opening (41) when the valve is in a closed position. In the open position the operations described in the preceding paragraph may take place (loading, unloading etc). Opening and closing may be achieved by adjusting the disc-equipped piston like device (44+45) and opening (41) relative each other so that liquid is able to pass or not to pass between disc (45) and the rim of opening (41).

The opening (39) in the end piece (13) is preferably ring-formed with opening (41) coaxially located inside it.

The openings (39) and (41) are preferably located centrally in the end piece (13).

Valve constructions having essentially the corresponding functionality can also be set up without a perforated plate or a mesh.

As illustrated in FIG. 5a, the outlet end of the reaction vessel may be equipped with a gel sensor (46) for determining/detecting the height of a fluidised bed and/or the bed homogeneity. This may often be appropriate because there will be advantages with running fluidised bode mode operations in the vessel with the valve (42) in an open position. By then controlling, for instance, bed height by the use of the signal from the gel sensor, it will be possible to adjust the flow velocity such that no significant amount of particles will escape out through opening (41).

The Tilting Aspect

In its broadest sense this aspect solves problem with respect to emptying vessels used in capturing a compound by particles in packed or fluidised bed mode.

A switch from fluidised bed mode to packed bed mode has easily been accomplished in the vessels used so far by allowing the particles to sediment and reverse the flow direction. This will hardly be feasible with the best variants of our novel distributor design.

The broadest aspect of the inventive tilting device comprises a vessel containing particles, either in fluidised bed or packed bed mode. A compound present in the in the liquid passing through the bed may then be captured by the particles. The vessel may be as described above, for instance in FIGS. 1–5, but may also be of a traditional type. The characterizing features are that the vessel a) has an end piece (13) at the top equipped with a valve (15), preferably located centrally, permitting loading and unloading the vessel etc, and b) is placed, for instance as illustrated in FIG. 5a, in a stand (47) permitting vertical tilting 180° from an upright position.

In order to facilitate vertical tilting the vessel may be equipped with one or more elements I (48) for attaching the vessel to the stand (47), and the stand (47) may be equipped with one or more elements II (49) for attaching the stand to the vessel. Elements I (48) may comprise shaft-like means or other support means for Elements II (49). Elements II (49) may comprise means that are complementary to the means of elements I (48), e.g. if elements I comprise shaft-like means then element II comprise support means fitting to the shaft-like means of elements I, or vice versa. An example of support means for shaft-like means is bear-rings.

A packed or fluidised bed in a suitable column/vessel placed in an upright position in the arrangement described in the previous paragraph can be tilted 180°. After tilting the vessel can be easily emptied by opening the top valve (15) (now at the bottom), possibly by flushing liquid into the vessel through the distributor (now at the top). In case the vessel is according to FIG. 5, flushing liquid through the mesh (37) (now at the bottom) may assist emptying, in particular in case the particles have caked or lumped together. Breaking up of cakes, lumps and the like may be further assisted by pulsing liquid flow into the vessel through valve (42) (with no flow entering the vessel through the distributor). In case the interior, side (14) of the end piece and, if present, also the mesh (37) and an optional perforated plate, are slightly conical as described in connection with FIG. 5, emptying will be further facilitated.

Vertical tilting 180° of vessel (8) placed in a stand (47) as described in connection with FIG. 5, will permit switching between fluidised bed and packed bed modes. See FIGS. 7a–d in which the distributor end is (50), the collector end (51), the fluidised bed (52) and the packed bed (53).

Figure 7A:
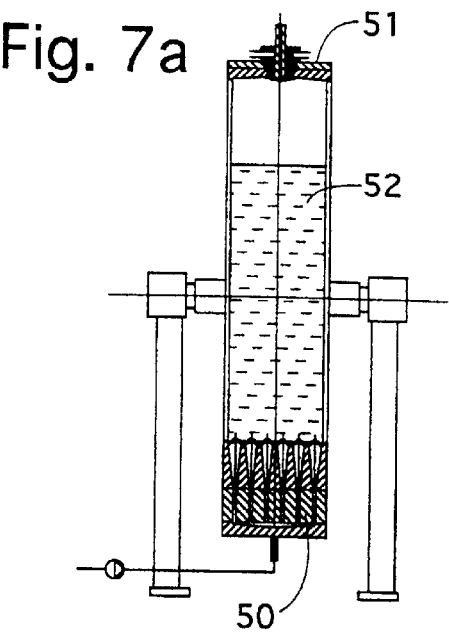
FIGS. 7a–d show a tiltable system in fluidised and packed bed modes with particles having densities greater than the fluid (FIGS. 7a–b, respectively) and with particles having densities less than the fluid (FIGS. 7c–d, respectively).
Figure 7B:
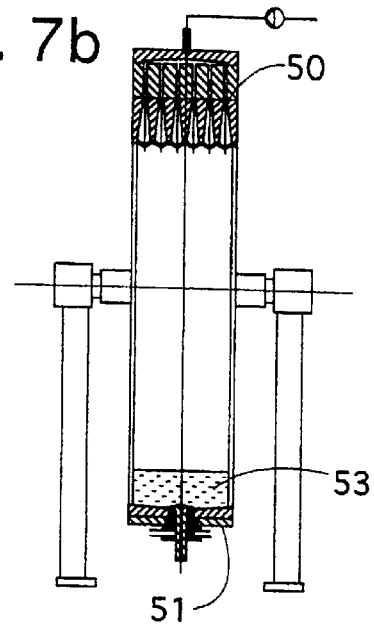

FIGS. 7a–b shows the case when the particles have a density that is greater than the flowing liquid. The fluidised bed (52) expands from the lower part of the vessel and the distributor (50) will be down (inlet end), the collector (51) up (outlet end) and the flow upward (FIG. 7a). The packed bed position is the reverse with distributor (50) up, collector (51) down and downward flow. The particles will sediment (53) at the collector end (FIG. 7b).

Figure 7C:
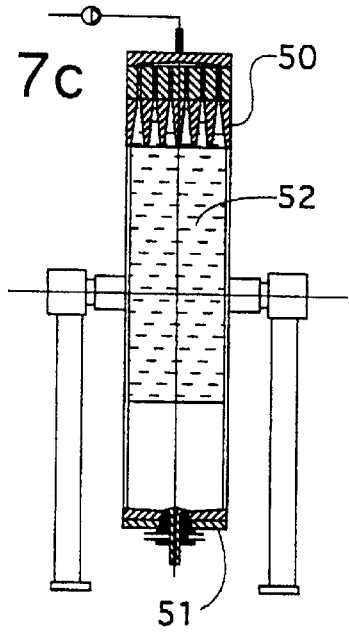
Figure 7D:
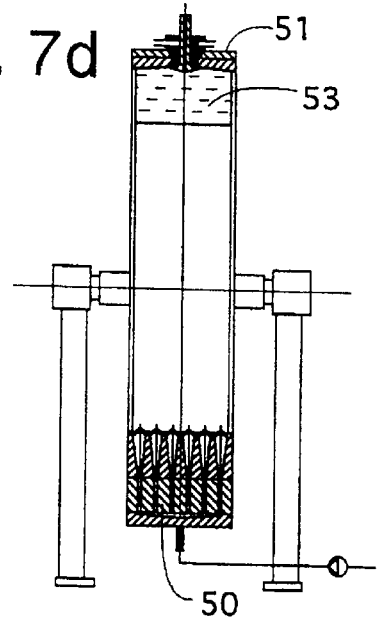

FIGS. 7c–d shows the case when the particles have a density that is lower than the flowing liquid. The fluidised bed (52) expands from above. The fluidised bed (52) position is with the distributor (50) up (inlet end), the collector (51) down (outlet end) and downward flow (FIG. 7c). The packed bed (53) position is the reverse with the distributor (50) down, the collector (51) up and upward flow. The particles will float and form a packed bed (53) beneath the collector end (51) (FIG. 7d).

Packed mode operations can be run directly after tilting from the fluidised bed position.

Other Column Arrangements Utilizing the Tilting Device of the Invention

The term "packed bed position" contemplates also a position in which particles are to be transferred from the tiltable vessel (vessel I) to a second vessel (vessel II). This latter vessel (II) is configured for packed bed treatment of the material (e.g. release, cleaning, regeneration etc) or permits physical separation of the particles from the liquid prior to letting them form a packed bed in still another vessel (vessel III). Vessels I and II may be connected to each other via a three-way valve in which a first port opens to vessel I, a second port to vessel II and a third port to the outside, for instance via a second three way valve to waste and buffer reservoirs.

Figure 8:
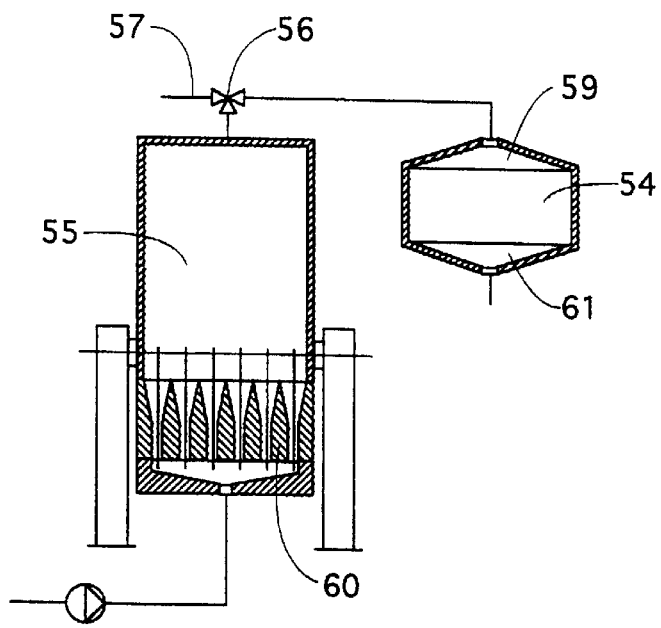
FIG. 8 shows a system containing two vessels: a first tiltable vessel I for fluidised bed mode and a second vessel II for packed bed mode.

FIG. 8 shows that vessel II (54) may be a conventional liquid chromatographic column that is physically apart from the tiltable vessel (vessel I) (55). In the figure the tiltable vessel I (55) is in a fluidised bed mode position and linked via a three-way valve (56) to vessel II (54). In the valve (56) one port is to vessel I, one to vessel II and one to an external tubing (57) that via an additional three-way valve may link the system to waste and buffer reservoirs, respectively. The collector arrangements (58 and 59) in vessel I and vessel II may be designed according to FIGS. 1–3 and 5 or as is well known in the art. The distributor arrangement (60) in vessel I and/or vessel II (61) may be of the conventional type with a distributor end piece, a distribution chamber, a mesh and possibly also a perforated plate. With respect to fluidised beds it is preferred to have the present inventive distributor design in vessel I. During fluidised bed operations the three-way valve (56) is closed to vessel II (54). When tilting vessel I (55), the three-way valve (56) is opened so that bed material can be transported between vessel I and II. The port to conduit (57) is closed. The content of vessel I (55) can now be flushed as described above which means that the particles and liquid ate transferred to vessel II (54).

In vessel II the particles are further processed, for instance in a release step and/or a washing step and/or a cleaning step and/or a regeneration step.

Figure 9:
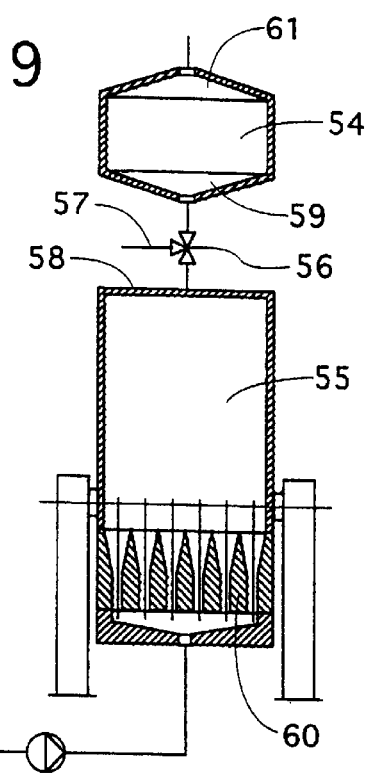
FIG. 9 shows a system in which there is a common tiltable integrated unit containing a first vessel I for fluidised bed mode and a second vessel II for packed bed mode.

FIG. 9 shows that vessel II (54) can be a conventional chromatographic column together with vessel I (55) form an integrated unit with one on top of the other (the bottom part of the stand is not shown). The connections between the vessels, inclusive valve arrangements, and collector and distributor arrangements may be according to FIG. 8. When the integrated unit containing vessels I and II is tilted vertically 180°, the port of the three-way valve (56) going to waste/buffer reservoirs is closed while the two other ports are opened. Vessel II (54) becomes below vessel I (55). The particles can be transferred to and treated in vessel II as described for FIG. 9.

Figure 10:
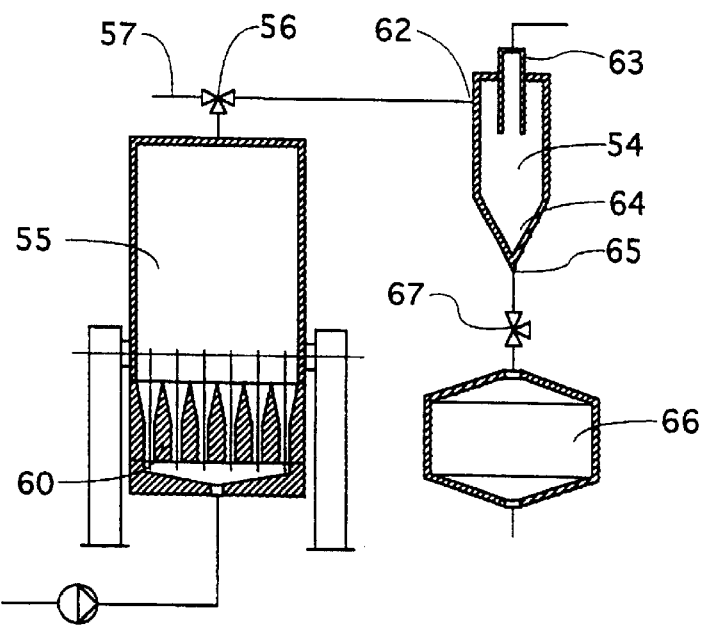
FIG. 10 shows a system in which there are a first tiltable vessel I for fluidised bed mode, a second vessel II in form of a hydrocyclone and a third vessel III for packed bed mode.

FIG. 10 shows that vessel II (54) may be a hydrocyclone. Vessel I (55) is in a fluidised bed position. If vessel I (55) is tilted to a packed bed position and the three-way valve (57) is open between vessel I (55) and the hydrocyclone (54), the particles plus the liquid in vessel I (55) can be transferred into the hydrocyclone (54) by flushing as described above. For particles having a density > the liquid, the selected hydrocyclone shall have an inlet at the top (62) through which the flow will enter the hydrocyclone cylinder tangentially thereby creating a vortex. Depending on flow rate, inlet area and diameter of the cylinder, the particles will be exposed for a number of gravity forces. This procedure will enable separation of the particles from dirty unwanted material, such as cells, cell debris and others. The unwanted material will leave the cylinder through the central top outlet (63) while the particles will fall down to the bottom (64) of the hydrocyclone.

To the bottom outlet (65) of the hydrocyclone (54) is suitably a third vessel/column (vessel III) (66) connected, preferably via a three-way valve (67). By having valve (67) open between hydrocyclone (54) and vessel III (66), the particles will be collected in vessel III. Subsequently release, cleaning, regeneration etc may take place, for instance by allowing the appropriate solutions to enter vessel III via the remaining port of the three-way valve (67).

Various Part Steps in Chromatographic Processes

Liquid chromatographic processes are carried out on particle matrices in form of packed or fluidised beds. The processes typically contain at least one step according to type 2 below and one or more steps selected among the remaining types of steps (1,3,4,5,6):

1) equilibrating the particles with a liquid conditioning the particles for capture/binding;
2) capturing one or more compounds present in a liquid sample by the particles;
3) washing the particles to which said one or more compounds have become bound;
4) releasing at least one of said one or more compounds from the particles;
5) cleaning the particles; and
6) regenerating the particles.

The capture step (type 2) together with the selected steps define an actual sequence in a chromatographic process. In an actual sequence there may also be steps other than those outlined above (1–6). Each step given above may be carried out either in fluidised bed mode or in packed bed mode. In an actual sequence there may be either or both of packed mode steps or fluidised mode steps.

In each step the particles are treated with an appropriate liquid (solution/buffer) that may be aqueous or non-aqueous.

In chromatographic processes comprising at least one step in fluidised bed mode, the equilibration, capture and washing steps are typically performed in fluidised bed mode. Releasing (for instance desorption) and cleaning and regeneration may be done in packed or fluidised bed mode.

Steps may wholly or partly coincide.

During the various steps the particles are placed in a vessel. Se also above. Chromatographic techniques comprise size exclusion (gel permeation) chromatography and adsorption techniques and techniques involving formation of covalent bonds between the particles and the compound to be removed from the liquid. Adsorption techniques are also called affinity chromatography. The important variants are ion exchange chromatography and techniques based on other affinity principles, such as bioaffinity, hydrophobic interaction (HIC), chelating interaction etc. The structure on the particles causing adsorption is often called affinity ligand or affinity structure.

Inventive Processes Utilizing Tilting

A first inventive process mode of the type described above comprises carrying out an actual sequence as defined above. The characterizing features are:

a) carrying out one of the steps of the actual sequence with a vertically placed vessel (8) having a valve (42) that in its open position provides direct access between the interior of the vessel (8) and an external tubing (43), said valve being located in the end that is directed upward during the step,
b) tilting the vessel vertically 180° after the step has been carried out,
c) opening the valve (42) and
d) emptying the vessel (8) through the valve (42).

The step referred to in (a) above may be any of the steps in the actual sequence. The emptying may be for carrying the bed material to waste or to be processed in another vessel, for instance as described in the context of tilting above. The reference numerals refer to FIGS. 5a–b.

A second inventive process mode is a process comprising an actual sequence as defined above containing at least one fluidised bed step and at least one packed bed step. The characterizing feature is that the vessel is tilted as described above when switching from a step performed in a fluidised bed mode to a step run in a packed bed mode or vice versa.

The switching between bed modes may mean transfer of the particles to another vessel, for instance as described above. Compare FIGS. 8–10.

The vessels used in these process modes may be vessels described above See FIGS. 3–5 and 7–10. The vessels may also carry previously known or future distributor arrangements, collector arrangements, predistributors etc. The vessel variants described above are preferred.

The end of the vessel that is directed upwards (top end) during fluidised bed operations may be equipped with a valve function providing direct access between the vessel interior and an external tubing when in an open position. This function is typically located centrally in the vessel end contemplated. See the valve described in the context of FIGS. 1–5 (reference numerals 15 and 42). See also FIGS. 7a–d.

After regeneration/equilibration of the particles in a packed bed position the vessel may be tilted to a fluidised bed position for initiating a second cycle of the same procedure. This second cycle then may start with a capture step in fluidised mode with a new batch of a liquid sample. An alternative may be to empty the vessel, for instance as described in the above-mentioned first process mode.

A third process mode is to perform an actual sequence of steps without utlizing tilting but using one or more of the inventive units described above. This mode follow rules well known in the field.

A fourth process mode utilizes increasing densities in the actual sequence of steps. This process is described in our copending International Patent Application deriving priority from SE 9803818-6 and SE 9803737-7 (which is hereby incorporated by reference).

In the above-mentioned process modes, the demands on particles, flow velocities, liquids etc are as known in the field.

The compound to be captured by the particles may be ions, for instance metal ions, and inorganic and organic compounds, for instance biomolecules, such as proteins, amino acids, nucleic acids, lipids, hormones etc.

The inventive aspects described herein thus will find uses within a large variety of technical fields, such as food industry, water purification, drug manufacturing, metal refining etc, The use of the inventive aspects described herein also encompasses binding processes other than those encompassing various aspects of purification. Exemplary other fields are inorganic as well as organic synthesis on particulate solid phases, reactors employing catalysts bound to particulate material etc. Examples of catalysts are enzymes and more or less complete biological systems.

Best mode: The best vessel experimentally tested is given in the experimental part ("Characterizing the stability of an expanded bed"). It is believed that this vessel will be improved in case a) the channels (7) are equipped with check valves as described in connection with FIGS. 5c–d, b) the widening outlet sections (7b) start with circular and end with squaric cross sectional areas [(17) FIGS. 5a–b; length 150 mm, 50 mm side of the squares at the outlet side (5) of the distributor block, widening angle 7°], and c) the widening angle (18) is increased next to the mouth of the widening outlet section (7b)

d) the widening angle is increasing at least at the lower part of widening section (7b).

The accompanying experimental part is only intended to illustrate the invention without intention to limit the same. The invention is further defined in the appending claims.

EXPERIMENTAL PART

Characterizing the Stability of an Expanded Bed

The vessel (300×300 mm, 1000 mm in height) had the novel distributor [6×6 channels (7) with a) narrow outlet sections (7a) having circular cross sectional areas, (diameter 3 mm; length 100 mm), b) widening outlet sections (7b) in forms of cones with their respective tip at the end of the narrow outlet sections and their base at the outlet side (5) of the distributor block (4) (length 150 mm, diameter 48 mm at their base), c) the area between the bases of the cones being sloped down into the respective cone (i.e. no area of the outlet side is perpendicular to the flow direction), widening angle (18)=7°, and d) no check valve.

No predistributor was included. The collector arrangement was conventional].

The vessel was filled with 11,3 liters of Streamline DEAE gel (Amersham Pharmacia Biotech AB, Uppsala, Sweden) having a particle size distribution in the range of 100–300 μm. The gel was expanded to 34 cm at a linear flow velocity of 300 cm/h (50 mM NaCl). The pressure drop across the distributor was 100 Pa. A positive step-response injection with 0.25% acetone solution was introduced into the column as a stimulus experiment. When 100% of the acetone solution could be detected at the column outlet, the flow was switched back to buffer solution for a negative step response. The plate number for the column (the bed+the above liquid) and the system was calculated on the basis of the negative in accordance with the same principle as that applied with pulse injection (Chemical Reaction Engineering, $2^{nd}$ Edition, John Wiley & Sons (1971)). The number of plates for the column plus system was 174. Compensation was then made for the number of plates for the system and the liquid above the bed. It was assumed that there was no dispersion at all in these parts of the equipment. With other words, all dispersion originated from the expanded bed. This is of course a worst case scenario. The number of plates for the bed was then 32. In turn, this corresponds to a V.D.N of $20 \times 10^{-3}$. True plug flow was thus well-established in the fluidised bed.

Test of Using Density Differences in Preventing Mixing Between Subsequently Incoming Liquids in a Liquid Fluidised Bed The background of this test is to be able to run the column in expanded mode throughout all the operating steps without loosing performance due to instability of the bed (mixing, channeling etc.). The theory was that the density of the liquids is the key factor whether two different liquids will mix or not in a fluidised bed and not the viscosity of the liquids. This means that a heavy liquid that is pumped into an expanded bed column (even distribution of liquid) which contains a lighter liquid, will create a sharp boundary between the two liquids and no mixing will occur. Whilst on the other hand, a light liquid pumped into a heavy liquid will cause severe mixing. By using increasing densities from liquid to liquid no mixing will occur and thereby a minimum of buffer consumption will be gained.

Experiment 1

The same vessel was used. No gel was used in this experiment. Five different liquids were pumped (at 300 cm/h) into the column from bottom to top in the following order:

| Liquid | Density | Comments |
| --- | --- | --- |
| 50 mM NaCl | 1.000 | |
| 5% (dry weight) yeast susp. | 1.015 | More viscous than 50 mM NaCl |
| 10.6% glycerol solution | 1.022 | More viscous than the yeast susp. |
| 0.82M NaCl | 1.030 | Less viscous than the glycerol solution. |
| 1.09M NaCl | 1.041 | More viscous than 0.82M NaCl |

The result was sharp boundaries between the different liquids and thereby no mixing of them. After having finished with 1.09 M NaCl, 50 mM NaCl was pumped into the column. The unfavourable density difference (light liquid into a heavier one) made the liquids to mix completely with each other.

This experiment illustrates that the liquid density is the governing factor when it comes to stable non mixing behaviour between different liquids.

What is claimed is:

1. A block for distributing liquid flow to an adsorption vessel (8), said block (4) comprising one inlet side (6) and one outlet side (5) that are parallel to each other, and therebetween, stretching from one side to the other, one or more parallel identical open channels (7) that are perpendicular to the two sides, wherein each channel (7) includes a narrow inlet section (7a) next to the inlet side (6) of the distributor block (4) and an outlet section (7b) which is widening towards the outlet side (5) of the block wherein the outlet side (5) of the block (4) is squaric and that opening of the widening outlet section is dense packed edge to edge in the outlet side, and that the vessel (8) has a squaric cross sectional area.

2. The block of claim 1, wherein each channel (7) includes a check valve.

3. The block of claim 2, wherein the check valve includes a check valve space (28) comprising a body (29) that is movable between a first position containing closing means (30) and a second position in which the body is retained by retaining means (31) while permitting liquid to pass through.

4. The block of claim 3, wherein the block (4) is positioned such that the channels (7) are vertically oriented with
   a) the flow direction is upward and the movable body (29) is selected to have a density greater than the density of the liquid or
   b) the flow direction is downward and the movable body (29) is selected to have a density less than the density of the liquid.

5. The block of claim 3, wherein the body (29) is spherical and the channel inlet (30) into the check valve space (28) has a circular cross sectional area with a diameter that is smaller than the diameter of the body, said channel inlet being the closing means (30).

6. The block of claim 1, wherein the narrow inlet section (7a) of the channel is capable of creating a pressure drop in the interval 10–10000 pascal when liquid is passing through.

7. The block of claim 1, wherein an angle (18) between the flow direction and the walls of the widening outlet section is greater than 2° but less than 15°.

8. The block of claim 1, wherein the vessel (8) contains a chromatographic matrix either in form of particles.

9. The block of claim 1, wherein the block (4) is modular in the sense that it comprises one or more identical block units (modules) (4a,b,c,d etc) that—are linked together edge-to-edge and contain one or more of the channels (7).

10. The block of claim 1, wherein the block on its inlet side (6) has a distributor chamber (9,9') that is capable of
    a) receiving liquid flow via one or more inlet conduits (2, FIGS. 1 and 2; and 3, FIGS. 3 and 5) and
    b) distributing the incoming liquid to the channels (7), with the provision that, when the distributor block is modular, each module has its own distribution block (4a,b,c,d . . .) and distribution chamber.

11. The block of claim 1, wherein each inlet opening (12, FIG. 11) is connected via pressure drop means (68a, 68a', 68b, 68b', FIG. 11) to a chamber (9') enabling liquid distribution to each inlet opening (12) via said means.

12. The block of claim 1, further comprising
    a) a predistributor with the pressure drop over the end flow passages (3) being at least 5 times the pressure drop created by the narrow inlet sections (7a) when liquid is flowing through the predistributor and the block, or/and
    b) sprinkler means (20) in the inlet openings (11) in the chamber(s) (9,9').

* * * * *